US012678252B2

(12) United States Patent
Klann

(10) Patent No.: US 12,678,252 B2
(45) Date of Patent: Jul. 14, 2026

(54) STERILE MONITOR AND DISPLAY COVERING FOR SURGICAL ENVIRONMENTS

(71) Applicant: Medline Industries, LP, Northfield, IL (US)

(72) Inventor: Kenneth James Klann, Willernie, MN (US)

(73) Assignee: Medline Industries, LP, Northfield, IL (US)

( * ) Notice: Subject to any disclaimer, the term of this patent is extended or adjusted under 35 U.S.C. 154(b) by 426 days.

(21) Appl. No.: 18/194,358

(22) Filed: Mar. 31, 2023

(65) Prior Publication Data

US 2023/0320803 A1    Oct. 12, 2023

Related U.S. Application Data

(60) Provisional application No. 63/326,890, filed on Apr. 3, 2022.

(51) Int. Cl.
*A61B 46/10*        (2016.01)
*A61B 46/00*        (2016.01)

(52) U.S. Cl.
CPC .............. *A61B 46/10* (2016.02); *A61B 46/40* (2016.02)

(58) Field of Classification Search
CPC .......... A61B 46/10; A61B 46/40; A61B 90/37
See application file for complete search history.

(56) References Cited

U.S. PATENT DOCUMENTS

| | | | |
|---|---|---|---|
| 5,429,142 A | 7/1995 | Szabo et al. | |
| 5,970,980 A | 10/1999 | Adair | |
| 6,132,367 A | 10/2000 | Adair | |
| 6,612,310 B2 | 9/2003 | Sklar | |
| 7,074,180 B2 | 7/2006 | Bertolero et al. | |
| 10,265,135 B2 | 4/2019 | Ghosh | |
| 2006/0065276 A1* | 3/2006 | Kammer | G05D 23/20 128/849 |
| 2008/0112842 A1 | 5/2008 | Edwards | |

(Continued)

FOREIGN PATENT DOCUMENTS

| | | |
|---|---|---|
| JP | 2015192791 A | 11/2015 |
| WO | 2017173465 A1 | 10/2017 |

OTHER PUBLICATIONS

International Search Report and Written Opinion in PCT/US2023/017168, 29 pages, Jul. 26, 2023.

*Primary Examiner* — Scott Luan

(74) *Attorney, Agent, or Firm* — SandBright, PLLC; Robert D. Spendlove

(57)        ABSTRACT

A drape can be used to cover a display device in a medical environment to create a sterile barrier over the display. The drape includes a front panel and a rear panel. The drape can form first and second top corner pockets and first and second bottom corner pockets. The drape may include a pull tab connected to one or both of the first and second bottom corner pockets. In use, a clinician can position the first and second top corner pockets of the drape over first and second upper corners of the display. The clinician can grasp the pull tab and pull the drape around the bottom edge of the display, positioning the first and second bottom corner pockets of the drape over the first and second bottom corners of the display. This can provide a tight fit between the drape and display for good visualization through the drape.

29 Claims, 12 Drawing Sheets

(56) References Cited

U.S. PATENT DOCUMENTS

| 2012/0232566 | A1 | | 9/2012 | Orban, III et al. |
| 2014/0261455 | A1 | | 9/2014 | Eastman et al. |
| 2022/0061947 | A1 | * | 3/2022 | Porter ................... A61B 50/00 |

* cited by examiner

PULL DRAPE OVER TOP
SIDE OF DISPLAY ~100

EXTEND DRAPE DOWN OVER
FRONT FACE OF DISPLAY ~102

PULL DRAPE OVER BOTTOM SIDE
OF DISPLAY USING PULL TAB ~104

STERILE MONITOR AND DISPLAY COVERING FOR SURGICAL ENVIRONMENTS

RELATED MATTERS

This application claims priority to U.S. Provisional Application No. 63/326,890, filed Apr. 3, 2022, the entire contents of which are incorporated herein by reference.

TECHNICAL FIELD

This disclosure relates to drapes and coverings used to provide a sterile barrier over medical equipment and, more particularly, to drapes and coverings for monitors and display devices.

BACKGROUND

The modern surgical suite is a highly complex and technically integrated operating environment. In the case of a surgical suite utilizing a surgical robotic system, for example, the surgical robot include one or more robotic arms that are manipulable by the clinician during the surgical procedure. The surgical robot can include various medical instruments insertable into the patient for performing the surgical procedure and may also include visualization aids, such as endoscopes, cameras, etc. to observe what is happening in and/or around the patient at the site of the surgical procedure. In either case, the surgical environment may include one or more electronic display devices presenting information to clinicians working in the environment. The electronic display devices may display video and/or still images of the procedure being performed to help the clinician manipulate the surgical robot, information concerning the status and performance of the surgical robot, or yet other information in the surgical environment.

Regardless of the configuration, various equipment within the surgical environment may be covered with a medical drape. A medical drape, also referred to as a surgical drape, can be used during surgical procedures to help protect equipment from contamination. For example, an equipment drape can be used to cover portions of a piece of medical equipment used during a procedure. This may include covering one or more monitors providing an electronic display in surgical environment. Use of draping can provide a physical barrier to help protect the surgical field from contamination, protecting the patient, clinicians, and/or equipment. The appropriate use of medical drapes can facilitate faster sterilization and turnaround of the operating room after a procedure and help minimize the possibility of cross-contamination and hospital acquired infection between procedures and patients.

SUMMARY

In general, this disclosure is directed to a drape for draping a display in a medical environment, including associated drape systems and draping techniques. The drape can provide a sterile barrier over the display in the medical environment. The display can be an electrically-powered computer monitor, television, or other display operable to display electronic content, such as images and/or information associated with a surgical procedure being performed in the medical environment. In one implementation, for instance, the display may be associated with (e.g., electrically connected to) a robotic surgical system and used to display information associated with a surgical procedure being performed by the robotic surgical system.

Independent of the configuration and intended use of the display in the medical environment, the drape can be positioned over the display to at least partially enclose the display in the material(s) forming the drape. This can provide a barrier layer between the surface of the display covered by the drape and an external environment, e.g., helping to prevent bodily fluid or other contaminants from the patient contacting the surface the display and/or any pathogens potentially present on the display from entering the patient.

In practice, it can be challenging to form a tight draping interface between the surface of the display being draped and the drape itself. If the drape is not tightly fitted to the display, such as merely placing a bag over the display, the drape can bunch and wrinkle across the face the display. This can distort visualization of the content displayed on the display through the drape, hindering a clinician's ability to effectively interpret and evaluate the information displayed on the display through the drape.

In accordance with some implementations of the present disclosure, a drape is provided that can facilitate a comparatively tight, fitted interface between the display being draped and the drape itself. For example, the drape may include a front panel positionable over a front face of the display and a rear panel positionable over at least a portion of the rear face of the display. The front and rear panels can be joined together, either directly or indirectly, to form corner pockets that can be inserted over the corners of the display. The drape can also include a pull tab graspable by a clinician draping the display. The clinician can grasp the pull tab and apply a force pulling the drape tightly on the display to form a comparatively tight interface between the front face of the display and at least the front panel of the drape.

For example, the drape may include one or more pull tabs associated with one or both bottom corner pockets of the drape. In one example, the drape includes a first pull tab extending from a first bottom corner pocket of the drape and a second pull tab extending from a second bottom corner of the drape. The one or more pull tabs may be connected to and/or formed from a section of material defining the rear panel of the drape.

In use, a clinician may position the drape over the top edge of the display. For example, the clinician may insert a first top corner pocket over a first top corner of the display and also insert a second top corner pocket over a second top corner the display. At the same time or thereafter, the clinician can bring the front panel of the drape down over the front face of the display. With the bottom corner pockets of the drape positioned generally coplanar with the bottom edge of the display, the clinician can grab a pull tab associated with one or both bottom corner pockets and pull one or both bottom corner pockets around the bottom corner(s) of the display. In the process of doing so, the clinician may tighten and/or stretch the front panel of the display to form a comparatively tight interface between the front panel of the drape in the front face the display. This may help remove wrinkles, bunching, and/or other nonconformities between the drape and front face the display. In either case, in some configurations, the clinician may pull the one or more pull tabs back along the rear face of the display, e.g., optionally pressing the one or more pull tabs against the rear face the display once the drape is pulled sufficiently tight to the display. In this way, the drape can be comparatively tightly fitted to the display being draped, e.g., while preventing excessive hand contact between the clinician and the drape and potential attendant loss of sterility.

In one example, a drape for covering a display in a surgical environment is described. The drape includes a front panel configured to be positioned over a front face of a display and a rear panel connected to the front panel, the rear panel being configured to be positioned over at least a portion of a rear face of the display. The drape also includes first and second top corner pockets and first and second bottom corner pockets. A first top corner pocket is formed between the front panel and the rear panel, the first top corner pocket being configured to be positioned over a first top corner of the display monitor. A second top corner pocket is formed between the front panel and the rear panel, the second top corner pocket being configured to be positioned over a second top corner of the display monitor. A first bottom corner pocket is formed between the front panel and the rear panel, the first bottom corner pocket being configured to be positioned over a first bottom corner of the display monitor. In addition, a second bottom corner pocket is formed between the front panel and the rear panel, the second bottom corner pocket being configured to be positioned over a second bottom corner of the display monitor. The example specifies that the drape includes at least one pull tab connected to at least one of the first bottom corner pocket and the second bottom corner pocket. The pull tab is graspable by a user to pull at least one of the first bottom corner pocket over the first bottom corner of the display and the second bottom corner pocket over the second bottom corner of the display.

In another example, a draped display is described. The example includes a display operable to display electronic content. The display has a rectangular shape that includes a first upper corner, a second upper, a first lower corner, and a second lower corner. The drape includes a front panel and a rear panel connected to the front panel. The drape defines first and second top corner pockets, first and second bottom corner pockets, and at least one pull tab connected to at least one of the first and second bottom corner pockets. The example specifics that the drape is positioned over the display with the front panel covering a front face of the display, the rear panel covering at least a portion of a rear face of the display, the first and second top corner pockets covering the first and second upper corners of the display, and the first and second bottom corner pockets covering the first and second bottom corners of the display. The example also specifies that the pull tab is pulled out and pressed against the rear face of the display.

In another example, a method of draping a display is described. The method includes pulling a drape over a top side edge of a display so the drape extends down over at least a portion of a front face and a rear face of the display and subsequently pulling the drape down over the front face of the display to cover the front face with the drape. The method further involves subsequently grasping a pull tab of the drape and using the pull tab to pull the drape around a bottom side edge of the display.

The details of one or more examples are set forth in the accompanying drawings and the description below. Other features, objects, and advantages will be apparent from the description and drawings, and from the claims.

DETAILED DESCRIPTION

This disclosure is generally directed to a drape for a display device, such as a computer monitor or television screen, used in a surgical environment. The display device may be a flat panel display that displays electronic media, e.g., still images, video images, electronic status and control information, and the like within a surgical environment. The display device may provide output from a robotic surgical device, output from an imaging device that images bodily content (e.g., fluoroscope, X-ray, CT), or yet other electronic output within a medical environment. In either case, the drape can be deployed over the display device to help create a sterile barrier between the face of the display device displaying electronic content and the surgical environment.

As will be described, some implementations of the drape include a front panel and a rear panel that are joined together, directly and/or with intervening sidewall panel(s), to form a structure positionable over the front face of a display as well as partially or fully over one or more sidewall regions of the display. For example, the drape may be positionable over some or all of the front face of the display and can wrap around one or more sidewall regions of the display to extend over some or all of the rear face the display. In some configurations, the drape includes corner pockets positionable over the corners of the display in addition to or in lieu of covering sidewall regions as a display extending between adjacent corners. In either case, the drape can include one or more pull tabs. The one or more pull tabs may be graspable by a clinician draping the display to help pull the drape over the display and stretch and/or tighten the drape relative to at least the front face of the display.

For example, in some configurations, the drape defines an interior receiving cavity having a substantially same shape as the shape of the display. For example, the display may typically have a rectangular or square shape, and the drape may define an interior cavity into which the display is intended to be inserted having a rectangular or square shape. In some implementations, the interior cavity of the drape is sized smaller than the size of the display in one or more dimensions (e.g., cavity height, cavity width, and/or cavity depth). When so configured, the clinician draping the display may stretch the drape to enlarge the size of the interior cavity as the drape is being placed over the display. The drape may be fabricated of one or more polymeric materials exhibiting elasticity having a tendency to draw the drape back toward its original size after being stretched. This can help form a tight fitment between the drape and the display.

Additional details on example drape configurations and method of draping are described in greater detail with respect to FIGS. 3-10. However, an example surgical environment and display that can be draped are described with respect to FIGS. 1 and 2.

Figure 1:
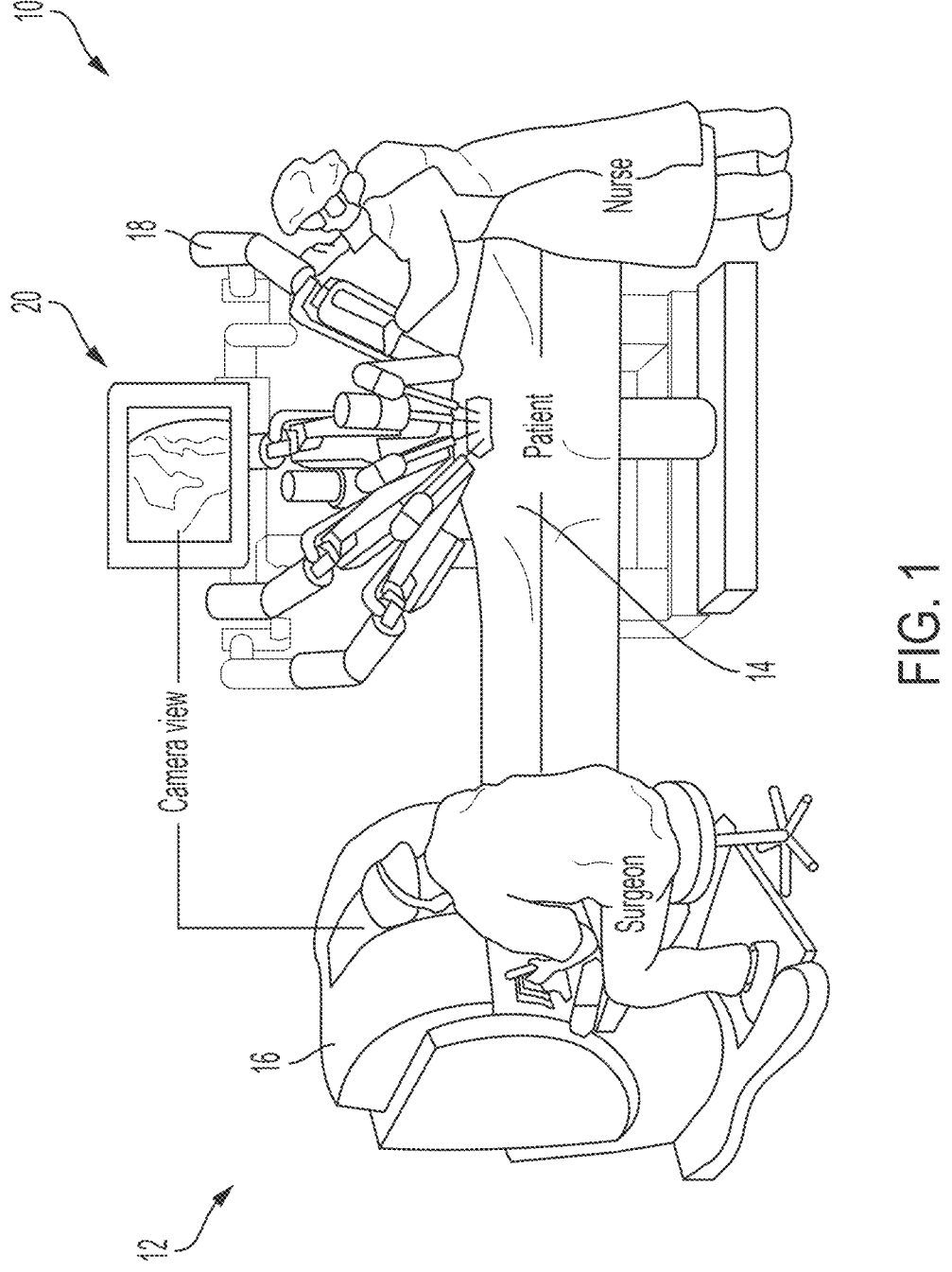
FIG. 1 is an illustration of an example surgical environment that that includes one or more displays that can be covered with a drape according to the disclosure.

FIG. 1 is an illustration of an example surgical environment that that includes one or more displays that can be covered with a drape according to the disclosure. In particular, FIG. 1 illustrates an example surgical environment 10 in which a robotic surgical system 12 is used to perform a surgical procedure on a patient 14. The example robotic surgical system 12 includes a surgeon control station 16, a patient-side robotic cart 18, and one or more displays 20. In use, a clinician can manipulate robotic surgical instruments carried by patient-side robotic cart 18 via surgeon control station 16 to perform a surgical procedure on patient 14. The one or more displays 20 can display electronic information concerning the surgical procedure being performed, such as images from inside body of the patient. The one or more displays 20 may be positioned on a standalone vision tower, on a desk, a wall-mounted surface, and/or any other desired location within the surgical environment.

Figure 2:
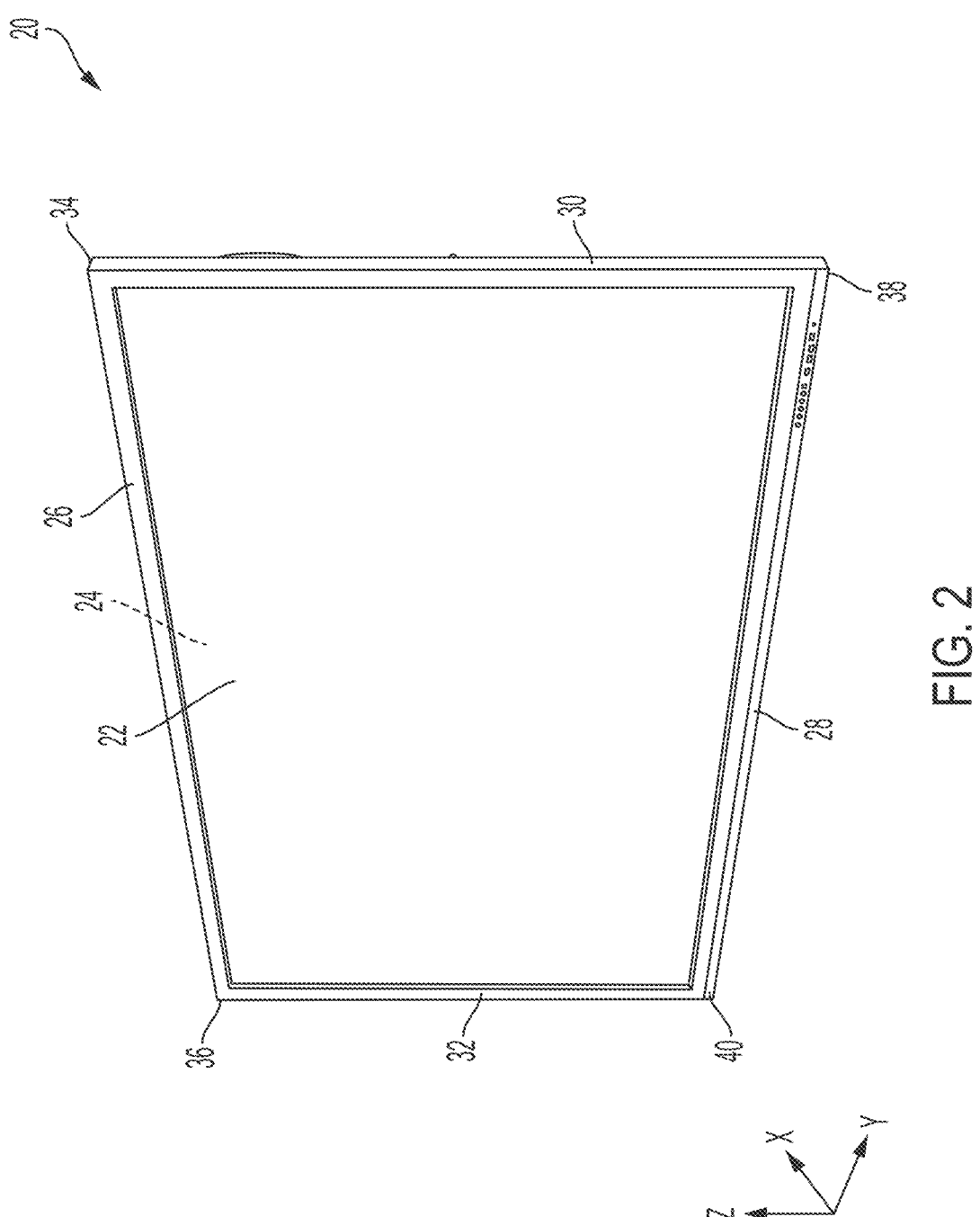
FIG. 2 is a perspective view of an example configuration of a display from FIG. 1 that can draped with a surgical drape according to the disclosure.

FIG. 2 is a perspective view of an example configuration of display 20 from FIG. 1 that can draped with a surgical drape according to the disclosure. Display 20 includes a front face 22 operable to display electronic content and a rear face 24 opposite the front face. Display 20 is illustrated as having a top edge 26 (also referred to as a top side edge), a bottom edge 28 (also referred to as a bottom side edge), of first side edge 30, and a second side edge 32. Top edge 26 intersects first side edge 30 to define a first top corner 34. Top edge 26 also intersects second side edge 32 to define a second top corner 36. Bottom edge 28 intersects first side edge 30 to define a first bottom corner 38. Bottom edge 28 also intersects second side edge 32 to define a second bottom corner 40. The regions of display 20 identified as being edges and corners may extend widthwise across the thickness of the display (in the X-direction indicated on FIG. 2) between front face 22 and rear face 24.

Display 20 can have a variety of different sizes and shapes, although most typically may have a square or rectangular shape. Further, while display 20 can have any thickness, the display may typically be implemented as a flat-panel display in which the thickness of the display (in the X-direction indicated on FIG. 2) is less than the width of the display (in the Y-direction indicated on FIG. 2) and the height of the display (in the Z-direction indicated on FIG. 2). For example, display 20 may have a thickness that is less than 20% of each of the width and the height of the display, such as less than 10% of each of the width and the height of the display. In various examples, display 20 may be a liquid crystal display (LCD), a gas plasma display, an electroluminescent (EL) display, a field emission display, or a digital micromirror device.

Figure 3A:
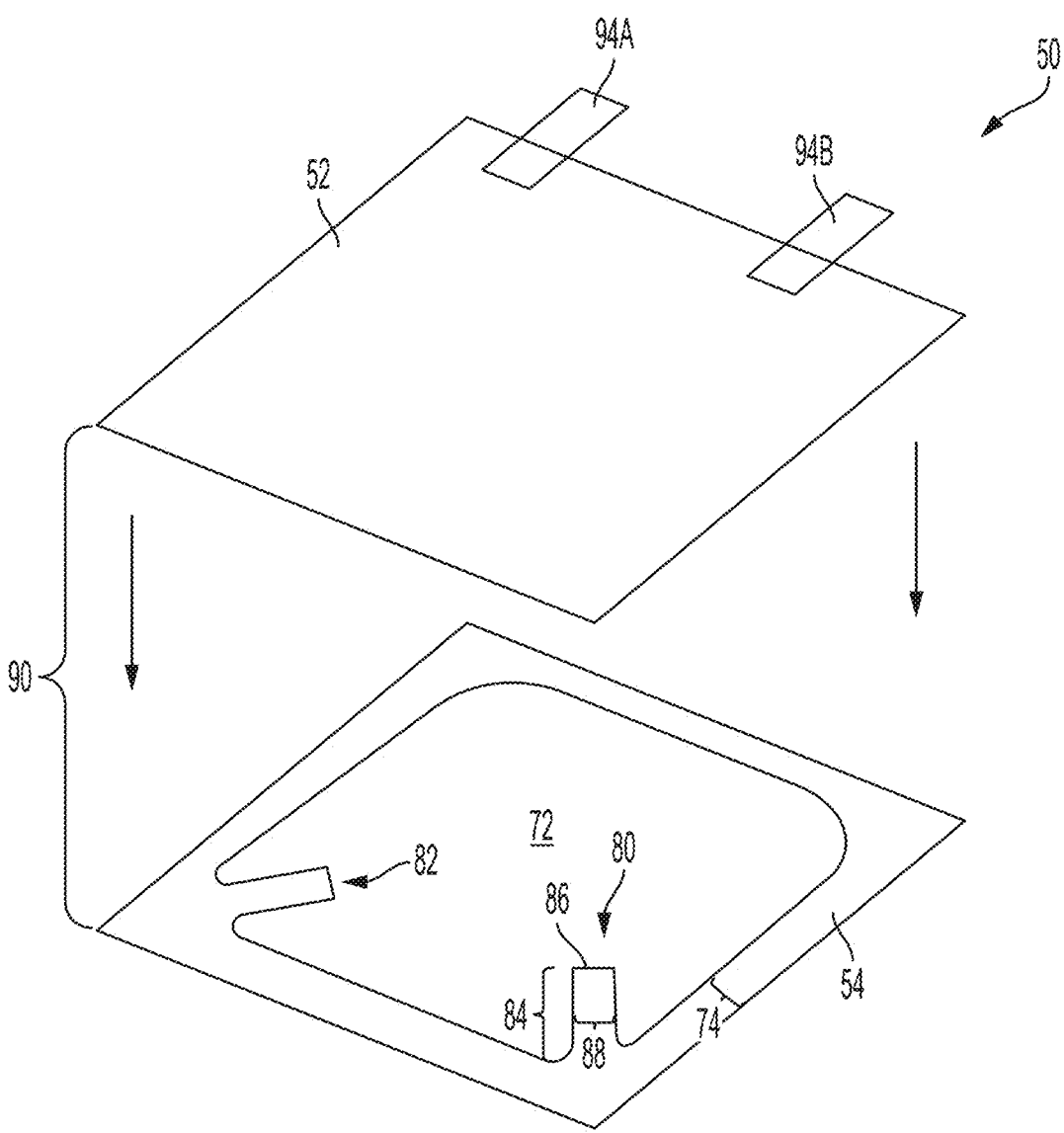
FIGS. 3A-3C are different perspective views of an example drape according to disclosure for draping a display.
Figure 3B:
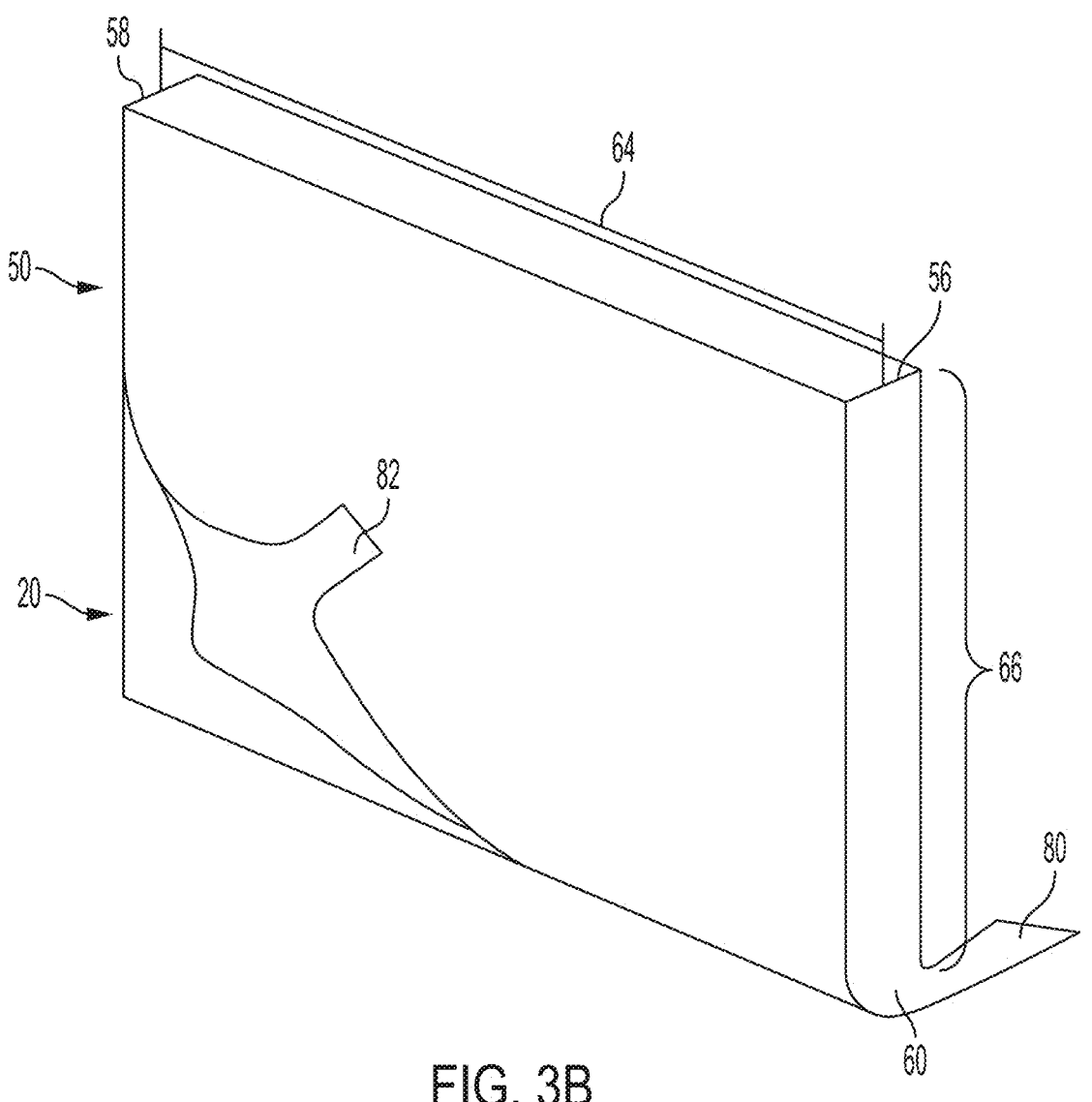
Figure 3C:
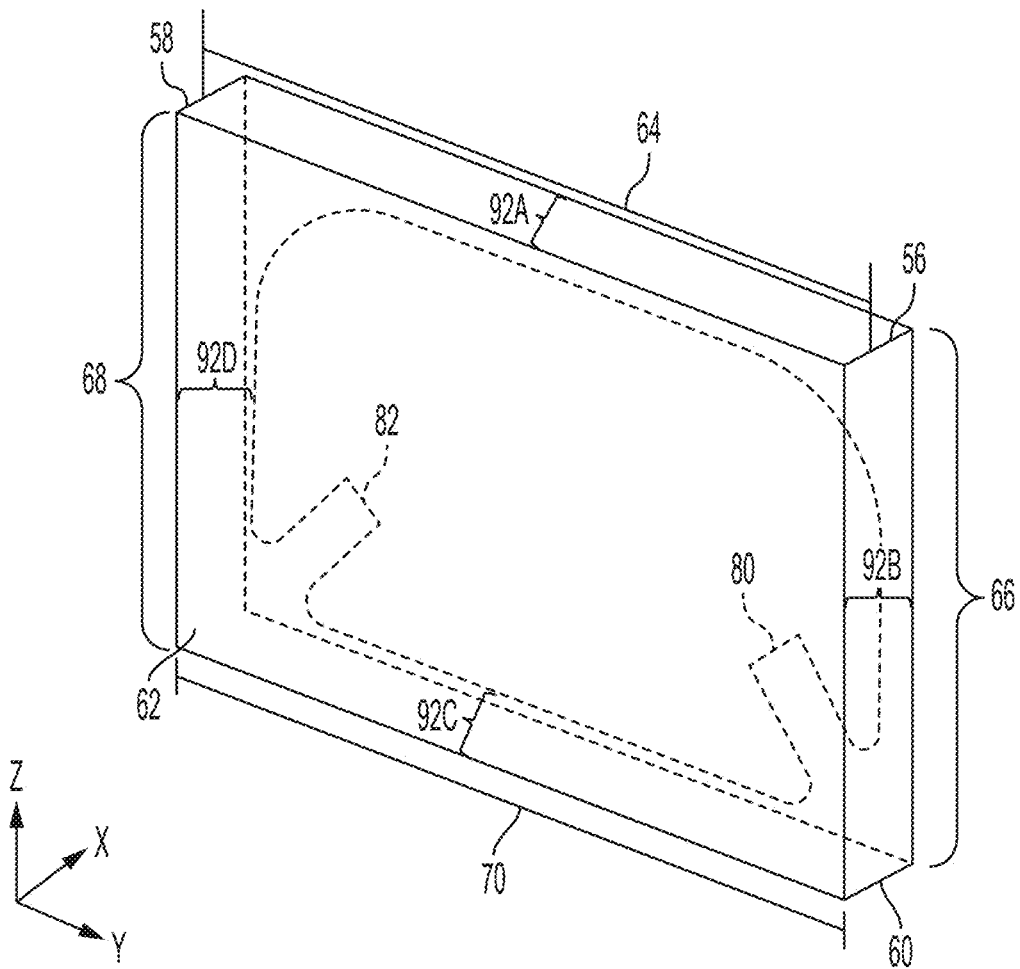

FIGS. 3A-3C (collectively referred to herein as "FIG. 3") are different perspective views of an example drape 50 according to disclosure for draping display 20. FIG. 3A illustrates a front panel 52 and a rear panel 54 of drape 50 being separated from each other but joinable together to form the drape. FIG. 3B is a front perspective view of drape 50 partially positioned over display 20. FIG. 3C is a front perspective view of drape 50 fully positioned over display 20 with dashed line portions of the figure illustrating structure on the rear side of the display. FIGS. 3A-3C collectively illustrate example structural features and configurations of drape 50 relative to display 20 to be draped.

In the illustrated example of FIG. 3, drape 50 can include a front panel 52 configured to be positioned over front face 22 of display 20 and a rear panel 54 configured to be positioned over at least a portion of rear face 24 of display 20. Front panel 52 and rear panel 54 can be joined together, either directly or indirectly via one or more intervening sidewalls. Drape 50 can be sized and/or shaped to be positioned over the corners and/or edges of display 20, e.g., with front panel 52 partially or fully covering the front face of the display and rear panel 54 partially or fully covering the rear face the display. As will be described in greater detail below, some configurations of drape 50 include one or more pull tabs to help facilitate installation of the drape over display 20.

Drape 50 can define a first top corner pocket 56 formed between front panel 52 and rear panel 54 configured to be positioned over first top corner 34 (FIG. 2) of display 20 and a second top corner pocket 58 formed between the front and rear panels configured to be positioned over second top corner 36 of the display. Drape 50 can also define a first bottom corner pocket 60 formed between front panel 52 and rear panel 54 configured to be positioned over first bottom corner 38 (FIG. 2) of display 20 and a second bottom corner pocket 62 formed between the front and rear panels configured to be positioned over second bottom corner 40 of the display.

The features of drape 50 described as being corner pockets may be regions of the drape positionable on and/or over edge sections of display 20 defining the corner of the display being draped. For example, a corner pocket of drape 50 may be positionable over a corner of display 20, e.g., such that the corner pocket contacts the opposed edges defining the corner of the display for anchoring the drape to the corner of the display. The corner pocket may also extend over at least a portion of the front face and/or rear face of the display. In some configurations, the corner pocket is closed with material such that, when the corner pocket is positioned over the corner of the display, the apex of the corner of the display is covered with the drape material. In other configurations, the corner pocket of the drape may define a cutout through which the apex of the corner of the display can project.

The individual corner pockets of drape 50 may be interconnected together by regions of the material forming the drape. For example, the individual corner pockets defined by drape 50 may be connected together by regions of material forming front panel 52 and/or rear panel 54. In some implementations, drape 50 defines one or more pockets configured to be positioned over one or more edges of display 20. Each pocket may be a region of drape material forming a cavity sized to receive an edge of display 20 therein. The cavity may have a depth corresponding to the thickness of the edge of the display to be inserted into the cavity. Each pocket may extend along the length and/or width of display 20, when drape 50 is fitted over the display, and form a region of material interconnecting adjacent corner pockets.

For example, drape 50 may define a top pocket 64 (FIG. 3B) configured to be positioned over top side edge 26 (FIG. 2) of display 20, a first side pocket 66 configured to be positioned over first side edge 30 of the display, a second side pocket 68 (FIG. 3C) configured to be positioned over second side edge 32 of the display, and/or a bottom pocket 70 configured to be positioned over bottom side edge 28 of the display. Depending on the configuration of drape 50, first side pocket 66 may intersect top pocket 64 to define first top corner pocket 56 and/or second side pocket 68 may intersect top pocket 64 to define a second top corner pocket 58. Additionally or alternatively, first side pocket 66 may intersect bottom pocket 70 to define first bottom corner pocket 60 and/or second side pocket 68 may intersect bottom pocket 70 to define second bottom corner pocket 62. Each pocket may wrap from front face 22 of display 20 around the edge of the display over which the pocket is positioned to rear face 24 of the display. In this way, the pocket may cover the edge of the display with material defining the drape along with regions of front face 22 and rear face 24 adjacent the edge covered by the pocket.

In some configurations, front panel 52 of drape 50 is a continuous sheet of material configured to completely cover front face 22 of display 20, e.g., without having openings resulting in any uncovered portion of the front face of the display after draping. Rear panel 54 of drape 50 may cover only a portion of rear face 24 of display 20 or may cover an entirety of the rear face of the display. In one implementation, rear panel 54 of drape 50 covers a portion of the rear face of the display but not an entirety of the rear face. For example, rear panel 54 of drape 50 may define one or more openings which, when the drape is positioned over display 20, result in one or more surfaces of the rear face 24 of display 20 being undraped. Such openings may be useful for a variety of reasons, such as to provide access to one or more connection ports of the display, facilitate routing of cabling, leave vent openings on the rear face the display uncovered for dissipating heat generated during operation of the display, and/or the like.

In the example of FIG. 3, rear panel 54 of drape 50 is illustrated as defining an open region 72 devoid of drape material (FIG. 3A). In the illustrated arrangement, rear panel 54 of drape 50 defines a section of material positionable around the perimeter of display 20 with the open region 72 being positioned inwardly from the perimeter of the display. For example, rear panel 54 of drape 50 may be configured to cover a portion of the rear face 24 of display 20 extending from an outermost edge of the rear face inwardly a distance 74 (e.g., optionally about an entire perimeter of the rear face the display). In various implementations, distance 74 may extend at least 5 cm from the outermost edge of the rear face 24 inwardly toward a center of the rear face, such as at least 10 cm, at least 20 cm, or at least 50 cm. For example, distance 74 may range from 10 cm to 100 cm.

In some configurations, the area of the rear face 24 of display 20 exposed through open region 72 divided by the total area of the rear face the display (the sum of the area exposed through open region 72 and the area covered by rear panel 54) is less than 0.75, such as less than 0.5, less than 0.25, or less than 0.10. For example, the ratio may range from 0.2 to 0.8, such as from 0.25 to 0.65.

When drape 50 defines pockets positionable over edges of display 20, the pockets may bound or delimit the open region 72 devoid of drape material. For example, the rear edge of top pocket 64, rear edge of first side pocket 66, rear edge of second side pocket 68, and/or rear edge of bottom pocket 70 may form boundaries defining open region 72 that is not covered with drape material.

As briefly introduced above, drape 50 can include at least one pull tab graspable by a user to help install the drape on display 20. For example, drape 50 may include at least one pull tab operatively connected to first bottom corner pocket 60 and/or second bottom corner pocket 62. During draping, a user can grasp the one or more pull tabs either individually or collectively to help pull the drape over first bottom corner 38 and/or second bottom corner 40. Additionally or alternatively, the user can grasp the one or more pull tabs to help tighten drape 50 on display 20, e.g., pulling front panel 52 substantially taut on front face 22 of the display.

In the illustrated example, drape 50 includes at least one pull tab, which is shown as being implemented as two pull tabs: a first pull tab 80 and a second pull tab 82. In the illustrated configuration, the one or more pull tabs are illustrated as being operatively connected to first bottom corner pocket 60 and second bottom corner pocket 62. In use, an individual draping display 20 can position first top corner pocket 56 and second top corner pocket 58 over respective top corners of display 20 and bring front panel 52 of drape 50 down over front face 22 of the display. The clinician can then grasp the one or more pull tabs to pull first bottom corner pocket 60 and second bottom corner pocket 62 over respective bottom corners of display 20. This can allow the user to stretch front panel 52 of drape 50 (e.g., downwardly with respect to gravity) parallel to and/or against front face 22 of display 20, helping to form a comparatively tight, wrinkle free interface between the drape and display surface. In addition, the one or more pull tabs provide a surface graspable by a user to manipulate drape 50 over display 20 while minimizing or eliminating potential contaminating contact between the user and front panel 52 of the drape.

Each feature described as a pull tab may be a structure directly or indirectly connected to a region of drape 50 that can be pulled or otherwise manipulated by applying a force to the pull tab. Each pull tab can be connected to a region of drape 50 to which a pulling force is desirably applied by a user during installation of the drape over display 20. In the illustrated configuration, the one or more pull tabs are operatively connected to first bottom corner pocket 60 and second bottom corner pocket 62. In particular, as illustrated, first pull tab 80 extends away from first bottom corner pocket 60, and second pull tab 82 extends away from second bottom corner pocket 62. In other configurations, a single pull tab maybe joined to and/or extend from both bottom corner pockets or only a single corner pocket (or yet other regions of drape 50). Additionally or alternatively, drape 50 may include one or more pull tabs connected to other features of the drape to help facilitate positioning over display 20. For example, drape 50 may include one or more pull tabs connected to first top corner pocket 56, second top corner pocket 58, top pocket 64, first side pocket 66, second side pocket 68, and/or bottom pocket 70 in addition to or in lieu of being operatively connected to one or both bottom corner pockets.

In the configuration of FIG. 3, first pull tab 80 and second pull tab 82 are each operatively connected to a section of rear panel 54 of drape 50 associated with a corresponding pocket portion defined by the drape. When so configured, each pull tab can be grasp by a user and pulled from front face 22 of display 20 to rear face 24 of the display. Once so repositioned, each pull tab may or may not be pressed against the rear face 24 of display 20 (e.g., causing the pull tab to cling to the rear face the display, such as through a static cling force) and be positioned substantially coplanar with a remainder of the rear panel 54 of drape 50.

As discussed above, drape 50 may or may not define an open region 72 devoid of drape material that is positionable over rear face 24 of display 20. In configurations in which drape 50 includes an open region 72, such as that illustrated, each of the one or more pull tabs 80, 82 may project from a respective bottom corner pocket into the open region. For example, as seen in FIGS. 3A and 3C, first pull tab 80 and second pull tab 82 can extend from respective bottom corner pocket 60, 62, angularly inwardly substantially toward a geometric center of rear panel 54. When projecting into open region 72, each pull tab may define a peninsula connected at one end to a remainder of rear panel 54 but otherwise surrounded by open region 72.

Each pull tab of drape 50 may define any suitable size and shape. In some implementations, a pull tab 80, 82 defines a length and a width, with the length of the pull tab being greater than the width. This can provide an elongated structure a user's hand can be wrapped around. For example, in the configuration of FIG. 3A, each pull tab is illustrated as defining a length 84 extending from a corner pocket to which the pull tab is connected to a terminal end 86. Each pull tab also defines a width 88 extending in a direction perpendicular to the length 84. In the illustrated arrangement, the length 84 is greater than the width 88. In one nonlimiting example, length 84 may be at least two times larger than width 88, such as at least four times larger. In some examples, drape 50 includes one or more pull tabs 80, 82 having a length 84 of at least 25 cm, such as at least 50 cm, at least 100 cm, or at least 150 cm.

In some examples, at least one (and optionally all) of the one or more pull tabs 80, 82 of drape 50 are formed of a same material as the material defining at least a portion of drape 50 (such as at least rear panel 54 of the drape). For example, the one or more pull tabs 80, 82 may be defined by a section of rear panel 54 of drape that extends from a remainder of the panel to provide the pull tab. When so configured, rear panel 54 may be a continuous sheet of material (optionally having void space 72 and/or other cutouts) that defines an integrally connected and unitary section of material forming the pull tab. In other configurations, the one or more pull tabs may be fabricated separately from a remainder of drape 50 (e.g., portions of rear panel 54) and thereafter connected to the drape. For example, the one or more pull tabs may be fabricated from a same polymeric material or a different material than a polymeric material forming drape 50 (e.g., rear panel 54 of the drape). Further, in some configurations, the one or more pull tabs may be detachably attached to a remainder of drape 50 such that the one or more pull tabs can be removed (e.g., torn off), as discussed in greater detail below with respect to example removable pull tab configurations.

Independent of the configuration of the one or more pull tabs 80, 82 defined by drape 50, the drape may be fabricated in a variety of different ways. In some examples, the drape is fabricated from a single sheet of material (e.g., folded over on itself to create front panel 52 and rear panel 54). In other examples, the drape is fabricated from two or more sheets of material joined together to form the resultant drape. The two or more sheets of material may be the same type of material or may be different types of material.

In some configurations, drape 50 may be fabricated from one panel of material forming front panel 52 and a second panel of material forming rear panel 54. In turn, front panel 52 and rear panel 54 may each be fabricated from a single sheet and/or type of material or multiple sheets and/or types of material joined together. In either case, front panel 52 and rear panel 54 may be directly or indirectly connected together.

In the example of FIG. 3A, for instance, drape 50 is illustrated as being formed from front panel 52 and rear panel 54 that are directly connected together to define a joint line 90. Joint line 90 can be established where an edge or other portion of front panel 52 is joined to a corresponding edge or other portion of rear panel 54. In the example of FIG. 3C, drape 50 is illustrated as being formed from front panel 52 and rear panel 54, with the two panels being indirectly connected together via one or more sidewall panels 92A-92D. In these types of examples, front panel 52 can be joined to one side of each sidewall panel 92 (e.g., forming a joint line between the front panel and sidewall panel) and rear panel 54 can be joined to another side of each sidewall panel 92 (e.g., forming a joint line between the rear panel and sidewall panel). The width of the sidewall panel 92 can define a separation distance between the front panel in the rear panel. Configuring drape 50 with one or more sidewall panels 92 between front panel 52 and rear panel 54 may provide a more form fitted drape to the shape of display 20.

When drape 50 is formed of multiple sections of material joined together, the various sections can be joined using any suitable techniques and/or elements to interconnect the sections of material. As one example, one or more sections of material forming drape 50 can be adhesively joined together using an adhesive composition. As another example, one or more sections of material forming drape 50 can be thermally bond together, e.g., by applying heat to melt bond one section of material to another section material. As still another example, one section material can be joined to another section material using one or more mechanical fixation elements, such as pins, snaps, hook and loop fasteners, and/or stitching.

In general, drape 50, including front panel 52 and rear panel 54, can be made of a sterile (and/or sterilizable) material that can be disposed of after a single use. Drape 50 may be typically fabricated from one or more types of polymeric material, such as polyvinyl chloride, polyethylene, polypropylene, polyurethane, polystyrene, and/or polycarbonate. After manufacture but before use, drape 50 may or may not be sterilized to ensure that the drape provides a sterile barrier between patient and display 20. For example, drape 50 may be subject to a sterilization process, such as steam sterilization, dry heat sterilization, ethylene oxide gas sterilization, or radiation sterilization.

In general, at least front panel 52 of drape 50 is fabricated from a substantially clear material, such as a visually transparent polymeric material. The material may be colored although, more commonly, may be uncolored. Configuring front panel 52 of drape 50 to be visually transparent can be beneficial to ensure that a clinician can view the content displayed on display 20 through the front panel, after the display is draped with drape 50.

In some implementations, drape 50 can include additional features to help attach and secure the drape to display 20. For example, drape 50 can include one or more sections of pressure sensitive adhesive disposed on a surface of the drape that can be pressed against a corresponding section of display 20 over which the drape is intended to provide protection. In other examples, drape is devoid of supplemental attachment or securing mechanisms, such as any pressure sensitive adhesive regions.

Drape 50 can be configured to have any desired size. In some implementations, drape 50 is sized and shaped complementary to the size and shape of display 20 over which drape 50 is intended to be installed. For example, drape 50 may be sized in one or more dimensions to correspond to the size of display 20 in those one or more dimensions. The size of drape 50 in those one or more dimensions may be less than ±25% of the size of display 20 in those one or more dimensions, such as ±20%, ±10%, or ±5%. In some examples, drape 50 is sized larger in one or more dimensions than the size of display 20 in those one or more dimensions, e.g., to help facilitate easy installation of the drape over the display. Additionally or alternatively, drape 50 may be sized smaller in one or more dimensions than the size of display 20 in those one or more dimensions.

For example, the cavity defined by drape 50 into which display 20 is to be inserted may be sized smaller than the size of display. For example, drape 50 may have a length, height, and/or depth before installation on display 20 smaller than a corresponding length, height, and/or depth of the display. The cavity may be sized smaller in one or more of a height dimension, a length dimension, and/or a thickness dimension than the corresponding dimensions of display 20. When so configured, the cavity defined by drape 50 can be stretched from its native size to conform to the specific dimensions of display 20 during installation. The drape may be fabricated from a material exhibiting elasticity that has a tendency to bias back toward its native size after being stretched to the size of display 20. In either case, the resulting stretch-fit installation can provide a tight interface between drape 50 (e.g., front panel 52 of the drape) and display 20 (e.g., front face 22 of the display), e.g., to help avoid wrinkles, bubbles, and/or other visual impairments associated with a comparatively loose draping of drape 50 over display 20. After being stretch fit over display 20, the size difference between drape 50 in one or more dimensions and the corresponding size of display 20 in those one or more dimensions may be less than 5%, such as less than 2%, less than 1%, less than 0.5%, or less than 0.25%.

As noted above, drape 50 can include one or more pull tabs positioned at various locations along the drape where force is desirably applied during installation of the drape. In some examples, drape 50 includes one or more top pull tabs 94A, 94B (FIG. 3A) associated with an upper portion of the drape and/or a side portion of the drape. For example, the one or more top pull tabs may be operatively connected to first top corner pocket 56, second top corner pocket 58, top pocket 64, and/or other regions of drape 50. The one or more top pull tabs may provide a structure that can be grasp by user to help manipulate an upper portion of drape 50 over corresponding upper regions of display 20, e.g., when initially positioning the drape on the display. This can allow the user to manipulate the drape while minimizing contact and contamination of other regions of the drape. Such one or more top pull tabs 94 can have any type of pull tab structure, e.g., as described herein.

In some configurations, the one or more top pull tabs are configured to be detachable from a remainder of drape 50 after use. For example, the one or more top pull tabs may be attached via adhesive, tearable stitching, and/or other fixation that allows the one or more pull tabs to be decoupled after use. When so configured, the user can grasp the one or more top pull tabs in use the tabs to help position drape 50 over display 20. When complete, the user can tear the one or more tabs off the remainder of the drape 50. In other configurations of drape 50 that include one or more top pull tabs, the one or more top pull tabs our permanently attached and not designed to be torn off after use.

An example technique for draping a display will be described with respect to FIGS. 4-10. The technique will be described in conjunction with display 20 and drape 50, although can be utilized using other display and drape configurations as described herein.

Figure 4:
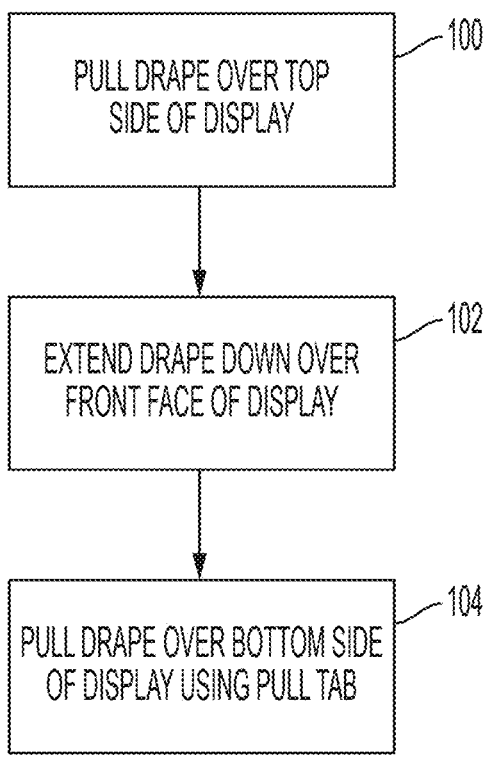
FIG. 4 is a flow diagram illustrating an example technique for positioning a drape on a display.

With reference to FIG. 4, the example technique includes pulling drape 50 over top side edge 26 of display 20 (100). For example, the user can position first top corner pocket 56 of drape 50 over first top corner 34 of display 20 and, either before, after, and/or simultaneously there with position second top corner pocket 58 of the drape over second top corner 36 of the display. In some configurations, the user may additionally or alternatively position a top pocket 64 defined by drape 50 over top side edge 26. During installation, the user can position at least a portion of front panel 52 of drape 50 over a portion of front face 22 of display 20 and/or at least a portion of rear panel 54 of drape 50 over a portion of rear face 24 of the display. In some and implementations, the user may grasp one or more pull tabs 94 in addition to or in lieu of grasping any other portion of drape 50 to help position the drape over top side edge 26 of display 20.

Figure 5:
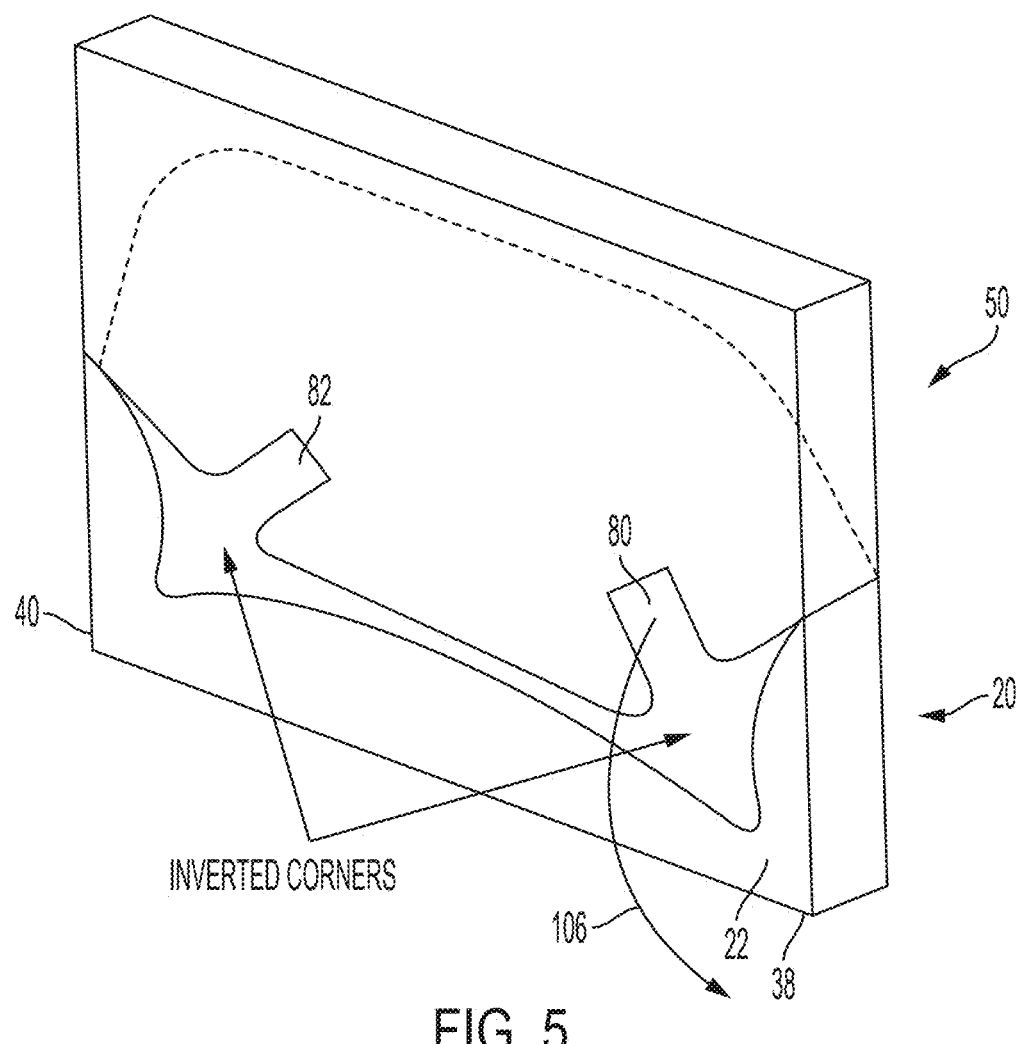
FIGS. 5-10 illustrate example steps for positioning the example drape of FIGS. 3A-3C over the example display of FIG. 2.

With drape 50 positioned over at least a portion of top side edge 26 of display 20, the user can pull front panel 52 down over front face 22 of the display to at least partially, and in some examples fully, cover the front face of the display with the drape (102). FIG. 5 is an illustration of an example configuration of drape 50 positioned on display 20 during installation in which the drape is positioned over the top side edge of the display and pulled down over the front face of the display. As shown in this example, the first and second pull tabs 80, 82 and corresponding first and second bottom corner portions are inverted (inside out) with the surface that will contact the rear face of the display after complete installation facing outwardly from the front face 22 of the display. In some such configurations, when the user pulls drape 50 down over front face 22 of display 20, the user may pull the drape down with the one or more pull tabs 80, 82 folded upwardly toward the top edge of the display.

The example technique of FIG. 4 involves the user grasping one or more pull tabs 80, 82 of the drape and using the pull tabs to pull the drape around the bottom side edge 28 of display 20 (104). The user can grasp the one or more pull tabs and pull the pull tabs around from being positioned on the front face of display 20 to being on the rear face of the display. For example, in the example of FIG. 5, the user may grasp first pull tab 80 and use the pull tab to pull drape 50 around first bottom corner 38 of the display in the direction indicated by arrow 106. In the process of pulling first pull tab 80 around first bottom corner 38, the user may position first bottom corner pocket 60 over first bottom corner 38.

Figure 6:
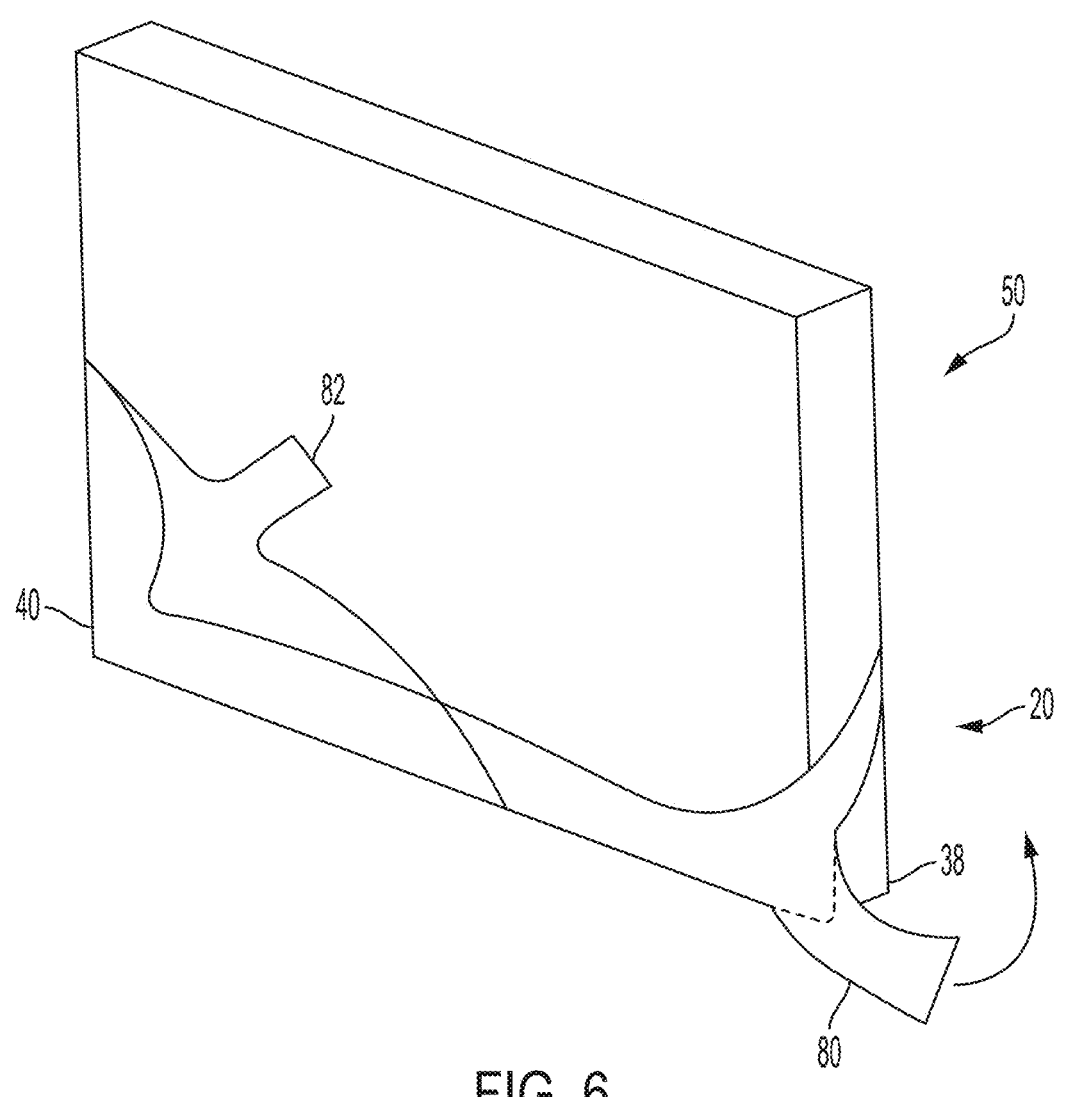
Figure 7:
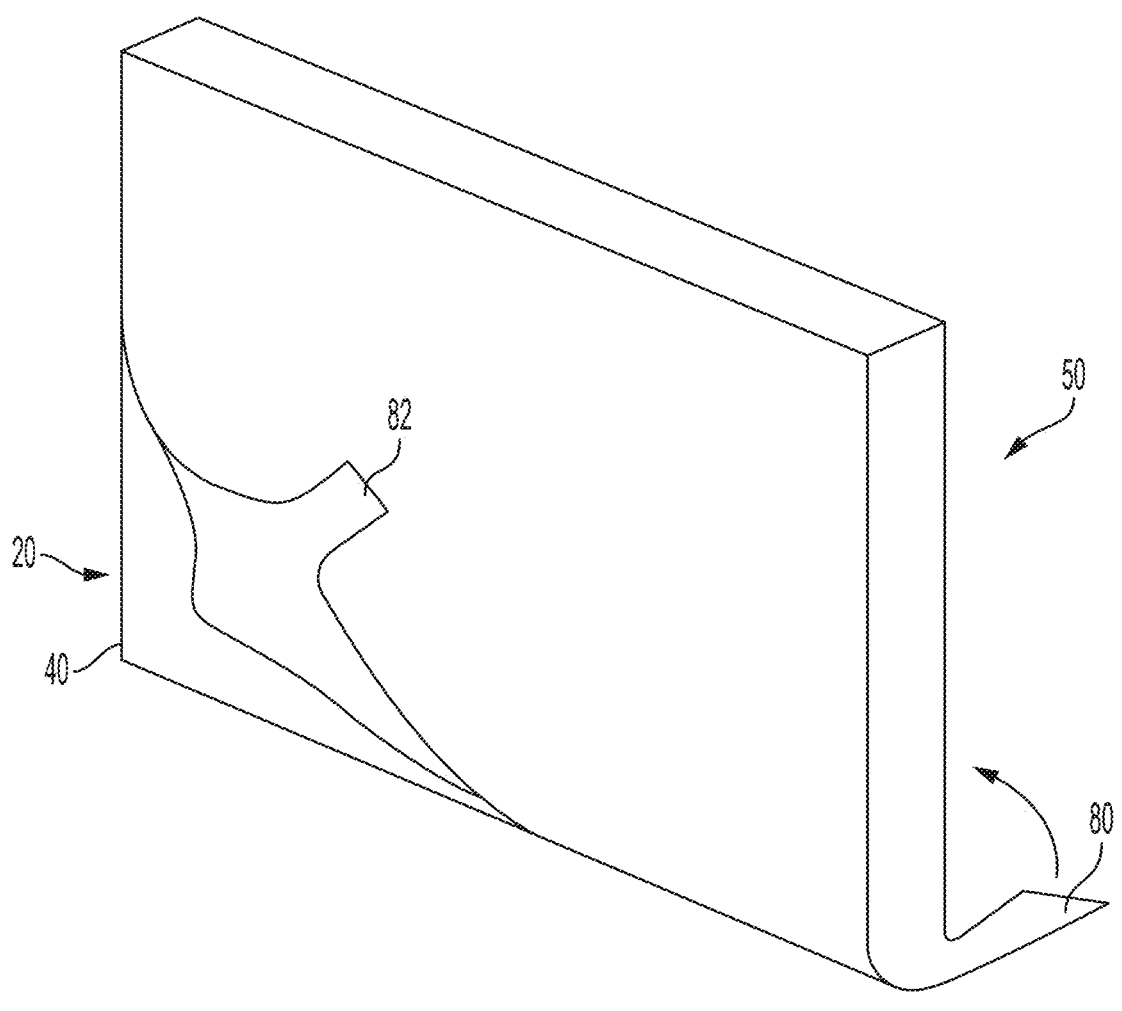
Figure 8:
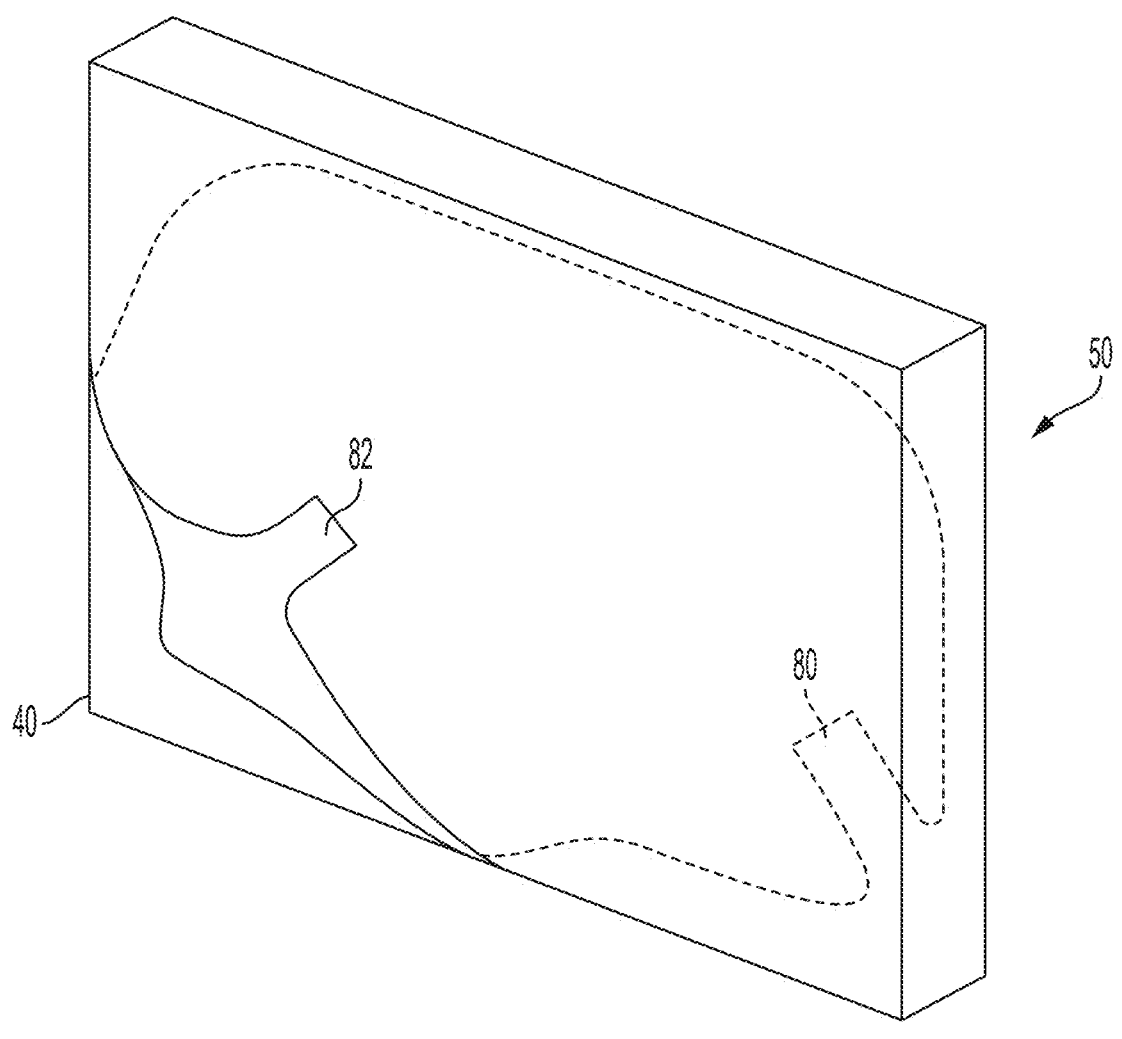

FIG. 6 illustrates of an example configuration of drape 50 during an example installation step on display 20 in which first pull tab 80 is being pulled around first bottom corner 38. After pulling first pull tab 80 around first bottom corner 38, the user may optionally press first pull tab 80 against the rear face 24 of display 20, as depicted in FIGS. 7 and 8.

Figure 9:
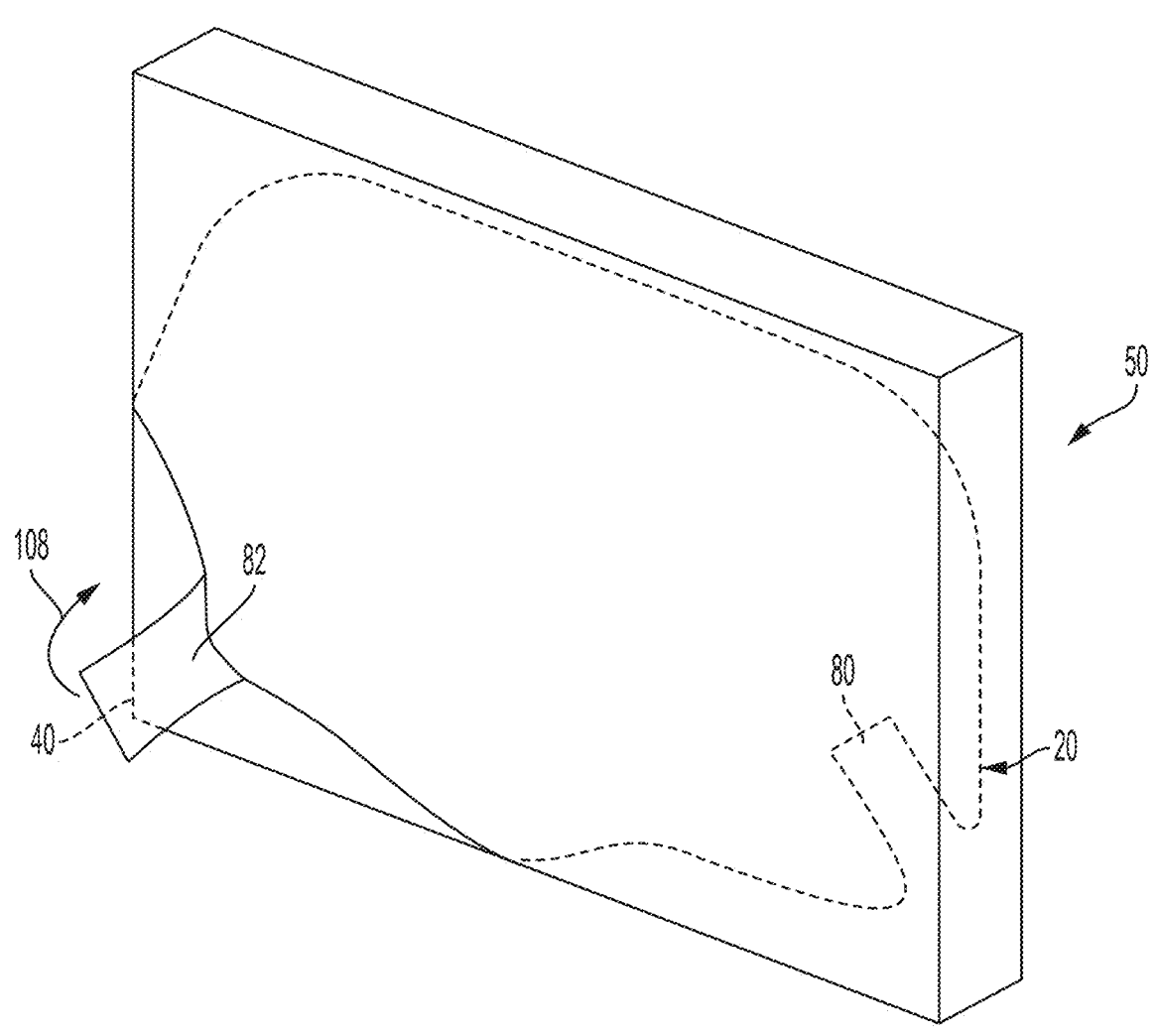
Figure 10:
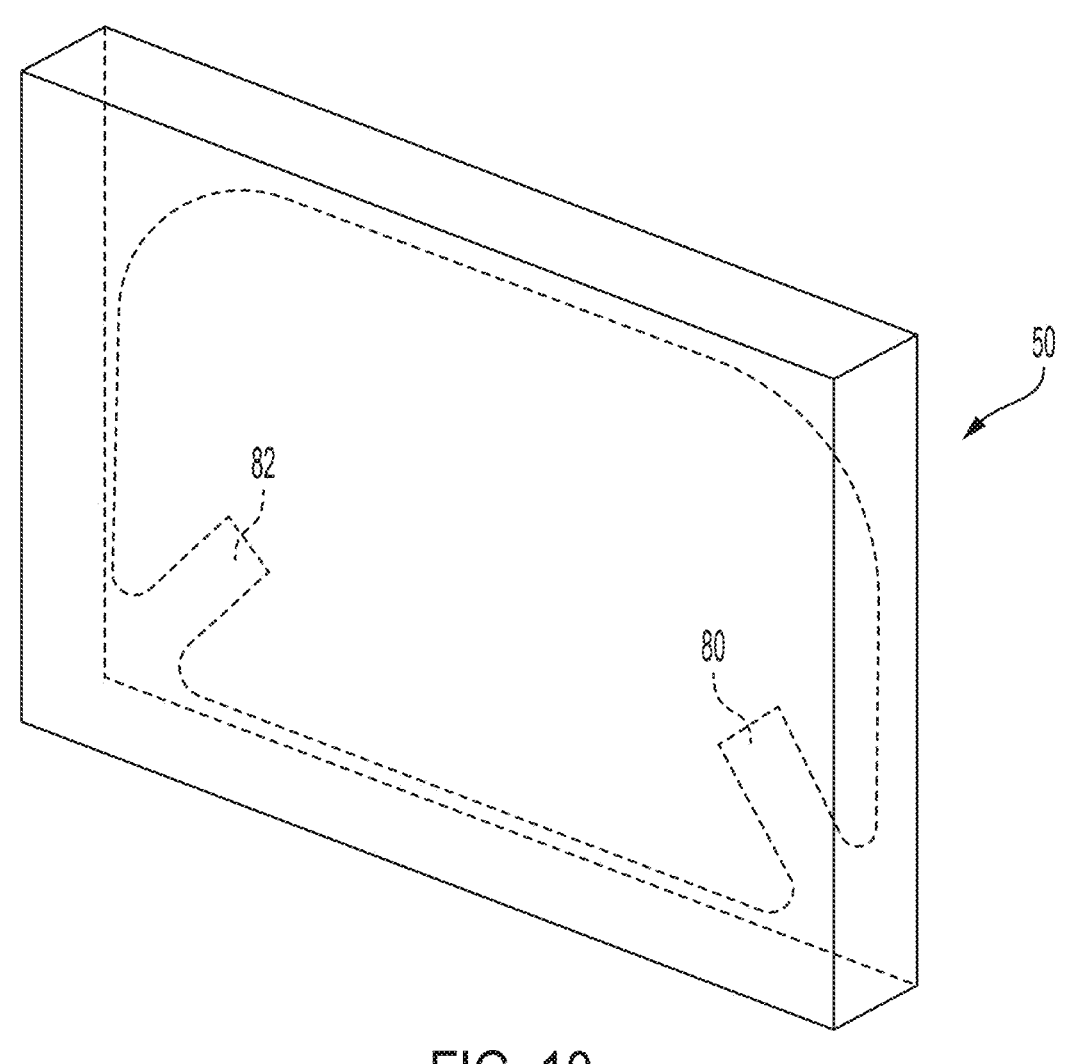

In configurations in which drape 50 includes multiple pull tabs, such as second pull tab 82, the user may also grasp second pull tab 82 and reposition the pull tab from being on the front face 22 of display 20 to being on the rear face 24 of the display. The user can reposition second pull tab 82 prior to, concurrent with, and/or after repositioning first pull tab. For example, the user may grasp second pull tab 82 and use the pull tab to pull drape 50 around second bottom corner 40 of the display. FIG. 9 is an illustration of an example configuration of drape 50 in which second pull tab 82 is being pulled in a direction indicated by arrow 108 to reposition the pull tab and hence portion of drape connected to the pull tab around the bottom edge 28 and/or second bottom corner 40 of the display. After pulling second pull tab 82 around second bottom corner 40, the user may optionally press second pull tab 82 against the rear face 24 of display 20, as depicted in FIG. 10.

By utilizing drape 50 with one or more pull tabs 80, 82 to help position the drape over display 20, the user can minimize or eliminate potentially contacting contact between the user's hands and front panel 52 of the drape. Additionally or alternatively, utilizing drape 50 with one or more tabs 80, 82 can help form a comparatively tight fitment and interface between the drape and display. This can reduce or eliminate wrinkles, bubbles, bunching, and/or discontinuities between front panel 52 of drape 50 and front face 22 of display 20, which can help improve viewing through information displayed on the display through the drape.

In some configurations, drape 50 is undersized compared to display 20 and stretchable (e.g., elastically stretchable) to conform to the size and/or shape of display 20. In these examples, the user can stretch drape 50 as the drape is positioned over display 20, e.g., stretching the drape in the direction of the height, length, and/or thickness of the display.

After positioning drape 50 over display 20, the resulting draped display system can be configured according to the discussion of display 20 and drape 50 herein. For example, the resulting draped display can include a display 20 operable to display electronic content, which may have a rectangular shape that includes a first upper corner, a second upper, a first lower corner, and a second lower corner. Drape 50, including front panel 52 and rear panel 54 connected to the front panel, can define first and second top corner pockets, first and second bottom corner pockets, and at least one pull tab connected to a portion of the drape. After installation, drape 50 is positioned over display 20, e.g., with front panel 52 covering front face 22 of the display and rear panel 54 covering at least a portion of rear face 24 of the display. The first and second top corner pockets can cover the first and second upper corners of the display and the first and second bottom corner pockets can cover the first and second bottom corners of the display. The least one pull tab can be positioned on a rear side of the display, such as pulled out (e.g., not folded over or compressed) and pressed against the rear face of the display.

It should be appreciated that the descriptive terms "top" and "bottom" with respect to the configuration and orientation of components described herein are used for purposes of illustration based on the orientation in the figures. The arrangement of components in real world application may vary depending on their orientation with respect to gravity. Accordingly, unless otherwise specified, the general terms "first" and "second" may be used interchangeably with the terms "top" and "bottom" without departing from the scope of disclosure.

Various examples have been described. These and other examples are within the scope of the following claims.

The invention claimed is:

1. A drape for covering a display in a surgical environment, the drape comprising:

a front panel configured to be positioned over a front face of a display;

a rear panel connected to the front panel, the rear panel being configured to be positioned over at least a portion of a rear face of the display;

a first top corner pocket formed between the front panel and the rear panel, the first top corner pocket being configured to be positioned over a first top corner of the display monitor;

a second top corner pocket formed between the front panel and the rear panel, the second top corner pocket being configured to be positioned over a second top corner of the display monitor;

a first bottom corner pocket formed between the front panel and the rear panel, the first bottom corner pocket being configured to be positioned over a first bottom corner of the display monitor;

a second bottom corner pocket formed between the front panel and the rear panel, the second bottom corner pocket being configured to be positioned over a second bottom corner of the display monitor; and at least one pull tab connected to at least one of the first bottom corner pocket and the second bottom corner pocket, the at least one pull tab being graspable by a user to pull at least one of the first bottom corner pocket over the first bottom corner of the display and the second bottom corner pocket over the second bottom corner of the display.

2. The drape of claim 1, wherein the at least one pull tab comprises a first pull tab connected to the first bottom corner pocket and a second pull tab connected to the second bottom corner pocket.

3. The drape of claim 1, wherein the at least one pull tab is defined by a section of the rear panel extending away from the at least one of the first bottom corner pocket and the second bottom corner pocket.

4. The drape of claim 1, wherein:

the rear panel defines an open region configured to be positioned over a portion of the rear face of the display that is offset from a perimeter of the display, the open region being devoid of drape material; and the at least one pull tab projects from the at least one of the first bottom corner pocket and the second bottom corner pocket into the open region.

5. The drape of claim 1, wherein the at least one pull tab define a length extending in a direction from the at least one of the first bottom corner pocket and the second bottom corner pocket to a terminal end and a width perpendicular to the length, and the length is greater than the width.

6. The drape of claim 1, wherein the at least one pull tab is configured to be pressed against the rear face of the display after being grasped by the user.

7. The drape of claim 1, wherein:

the rear panel is connected to the front panel to form a top pocket configured to be positioned over a top side edge of the display, a bottom pocket configured to be positioned over a bottom side edge of the display, a first side pocket configured to be positioned over a first side edge of the display, and a second side pocket configured to be positioned over a second side edge of the display;

the first side pocket intersects the bottom pocket to form the first bottom corner; and the second side pocket intersects the bottom pocket to form the second bottom corner.

8. The drape of claim 7, wherein:

the at least one pull tab comprises a first pull tab and a second pull tab;

the first pull tab projects angularly inwardly from the first bottom corner; and the second pull tab projects angularly inwardly from the second bottom corner.

9. The drape of claim 7, wherein the top pocket, the bottom pocket, and first side pocket, and the second side pocket are each configured to be positioned over the portion of the rear face of the display and delimit an open region devoid of drape material.

10. The drape of claim 7, wherein the rear panel is directly connected to the front panel along a joint line.

11. The drape of claim 7, wherein the rear panel is indirectly connected to the front panel with at least one sidewall panel positioned between the rear panel and front panel.

12. The drape of claim 11, wherein the front panel and the rear panel are each formed of a same polymeric material.

13. The drape of claim 1, wherein:

the display over which the drape is configured to be installed has a length and a height;

the drape defines a length and a height; and the length and the height of the drape prior to installation is less than the length and the height of the display, respectively, to facilitate stretch-fitting of the drape during installation.

14. The drape of claim 1, further comprising at least one top pull tab connected to at least one of the first top corner pocket and the second top corner pocket, the at least one tear tab being graspable by a user to pull at least one of the first top corner pocket over the first top corner of the display and the second top corner pocket over the second top corner of the display.

15. The drape of claim 1, wherein the at least one top pull tab comprises a tear tab configured to be torn off after use.

16. A draped display comprising:

a display operable to display electronic content, the display having a rectangular shape comprising a first upper corner, a second upper, a first lower corner, and a second lower corner; and a drape comprising a front panel and a rear panel connected to the front panel, the drape defining first and second top corner pockets, first and second bottom corner pockets, and at least one pull tab connected to at least one of the first and second bottom corner pockets, wherein the drape is positioned over the display with the front panel covering a front face of the display, the rear panel covering at least a portion of a rear face of the display, the first and second top corner pockets covering the first and second upper corners of the display, the first and second bottom corner pockets covering the first and second bottom corners of the display, and the least one pull tab is positioned on the rear face of the display.

17. The draped display of claim 16, wherein the at least one pull tab comprises a first pull tab connected to the first bottom corner pocket and a second pull tab connected to the second bottom corner pocket, and both the first pull tab and the second pull tab are pulled out and pressed against the rear face of the display.

18. The draped display of claim 16, wherein:

the rear panel defines an open region positioned over a portion of the rear face of the display that is offset from a perimeter of the display, the open region being devoid of drape material; and the at least one pull tab projects into the open region.

19. The draped display of claim 16, wherein:

display comprises a top side edge, a bottom side edge, a first side edge, and a second side edge;

the drape comprises a top pocket, a bottom pocket, a first side pocket, and a second side pocket, the first side pocket intersecting the bottom pocket to form the first bottom corner and the second side pocket intersecting the bottom pocket to form the second bottom corner; and the top pocket of the drape is positioned over the top side edge of the display, the bottom pocket is positioned over the bottom side edge of the display, the first side pocket is positioned over the first side edge of the display, and the second side pocket is positioned over the second side edge of the display.

20. The draped display of claim 19, wherein:

the at least one pull tab comprises a first pull tab and a second pull tab;

the first pull tab projects angularly inwardly from the first bottom corner; and the second pull tab projects angularly inwardly from the second bottom corner.

21. The draped display of claim 19, wherein the top pocket, the bottom pocket, and first side pocket, and the second side pocket are each positioned over the portion of the rear face of the display and delimit an open region on the rear face of the display devoid of drape material.

22. The draped display of claim 16, wherein:

the display has a length and a height;

the drape defines a length and a height; and the drape is stretch-fit over the display to conform the length and the height of the drape to the length and the height of the display, respectively.

23. The draped display of claim 16, wherein the display is a flat-panel display having a rectangular shape.

24. A method of draping a display, the method comprising:

pulling a drape over a top side edge of a display so the drape extends down over at least a portion of a front face and a rear face of the display;

subsequently pulling the drape down over the front face of the display to cover the front face with the drape; and subsequently grasping a pull tab of the drape and using the pull tab to pull the drape around a bottom side edge of the display.

25. The method of claim 24, wherein using the pull tab to pull the drape around the bottom edge of the display comprises positioning the pull tab from the being on the front face of the display to being on the rear face of the display.

26. The method of claim 24, wherein the pull tab comprises a first pull tab and a second pull tab, and grasping the pull tab comprises grasping the first pull tab and using the first pull tab to pull the drape around a first bottom corner of the display and grasping the second pull tab and using the second pull tab to pull the drape around a second bottom corner of the display.

27. The method of claim 24, further comprising, after using the pull tab to pull the drape around a bottom side edge of the display, pressing the pull tab against the rear face of the display.

28. The method of claim 24, wherein pulling the drape over the top side edge of the display comprises grasping a top pull tab and using the top pull tab to pull the drape over the top side edge of the display.

29. The method of claim 28, further comprising tearing the top pull tab off the drape.

* * * * *